United States Patent [19]

Neidhard et al.

[11] 4,007,589
[45] Feb. 15, 1977

[54] INTERNAL COMBUSTION EXHAUST CATALYTIC REACTOR MONITORING SYSTEM

[75] Inventors: Horst Neidhard, Korntal; Ernst Linder, Muhlacker; Josef Wahl, Stuttgart; Peter Jürgen Schmidt, Schwieberdingen, all of Germany; Peter A. Schoeck, Balzers, Liechtenstein

[73] Assignee: Robert Bosch G.m.b.H., Stuttgart, Germany

[22] Filed: Feb. 20, 1976

[21] Appl. No.: 659,716

Related U.S. Application Data

[62] Division of Ser. No. 436,863, Jan. 28, 1974, Pat. No. 3,962,866.

[30] Foreign Application Priority Data

Jan. 31, 1973 Germany .......................... 2304622

[52] U.S. Cl. .................................. 60/276; 60/277; 60/278
[51] Int. Cl.² .......................................... F01N 3/15
[58] Field of Search ............ 60/276, 277, 278, 295; 23/288 FR

[56] References Cited

UNITED STATES PATENTS

| | | | |
|---|---|---|---|
| 3,072,457 | 1/1963 | Bloch | 60/295 |
| 3,441,381 | 4/1969 | Keith | 60/276 |
| 3,696,618 | 10/1972 | Boyd | 60/276 |
| 3,766,536 | 10/1973 | Hile | 60/277 |
| 3,768,259 | 10/1973 | Carnahan | 60/276 |
| 3,785,151 | 1/1974 | Holl | 60/277 |

Primary Examiner—Douglas Hart
Attorney, Agent, or Firm—Flynn & Frishauf

[57] ABSTRACT

To supervise operational effectiveness of catalytic reactors included in exhaust emission detoxification systems, an oxygen sensor is located downstream of the reactor to determine oxygen content in the exhaust gases from the internal combustion engine, the oxygen sensor comprising an ion conductive solid electrolyte forming an ion concentration chain and having catalytically inactive contacts, connected to a detection circuit which provides an output signal in dependence on a signal from the sensor, the output signal operating an alarm, or a transducer which interferes with proper engine operation to force the operator to have the reactor repaired. Preferably, two ion conductive chains are used, in a single sensor, or in two sensors, one being exposed to exhaust gases upstream of the catalytic reactor and the other downstream of the catalytic reactor, the output signals being provided to a differentially connected operational amplifier, to balance out extraneous influences.

12 Claims, 7 Drawing Figures

INTERNAL COMBUSTION EXHAUST CATALYTIC REACTOR MONITORING SYSTEM

CROSS REFERENCE TO RELATED PATENTS

This is a division of application Ser. No. 436,863, filed Jan. 28, 1974, now U.S. Pat. No. 3,962,866.

U.S. Pat. No. 3,874,171

U.S. Ser. No. 259,157, filed June 2, 1972, Schmidt et al.

U.S. Pat. No. 3,851,469

The present invention relates to a system to monitor the activity, and effectiveness of catalytic reactors in the exhaust emission detoxification system connected to internal combustion engine exhaust systems.

Catalytic reactors are suitable to detoxify exhaust gases from internal combustion engines. The effectiveness of detoxification, that is, the control of pollution due to the exhaust gases depends on the operating effectiveness of the catalytic reactor. The operation of the system, including the catalytic reactor must be monitored. The loss of activity of the reactor is one of the main reasons for failure of the detoxification system. The loss of activity depends on the time-temperature loading on the catalytic reactor, that is, on the loading and the operating time of the internal combustion engine. Ordinarily, the detoxification effectiveness of the catalytic reactor cannot be noticed by checking the operation of the internal combustion engine as such, and the driving characteristics of the vehicle, or the operating characteristics of the engine do not change with change in efficiency of operation of the detoxification system.

It is an object of the present invention to provide a supervisory or monitoring system to check or monitor the activity of a catalytic reactor in the detoxification system of the exhaust gases of internal combustion engines. An output indication is obtained if the catalytic reactor does not have its design effectiveness; the operating characteristics of the vehicle may, also, be interfered with to force the operator of the vehicle to replace, or repair the catalytic reactor.

SUBJECT MATTER OF THE PRESENT INVENTION

Briefly, sensor elements are exposed to exhaust gases upstream, and downstream of the catalytic reactor respectively, sensing the oxygen content of the exhaust gases from the internal combustion engine. The sensor elements include an ion conductive solid electrolyte with an oxygen concentration chain with catalytically inactive contacts applied to the solid electrolyte; a difference circuit is connected to the sensor which, in dependence on the output signals from the sensor elements operates a warning device, or a transducer which affects operation of the internal combustion engine, and hence the operation of the vehicle of which it may form a part.

The invention will be described by way of example with reference to the accompanying drawings, wherein.

Figure 1:
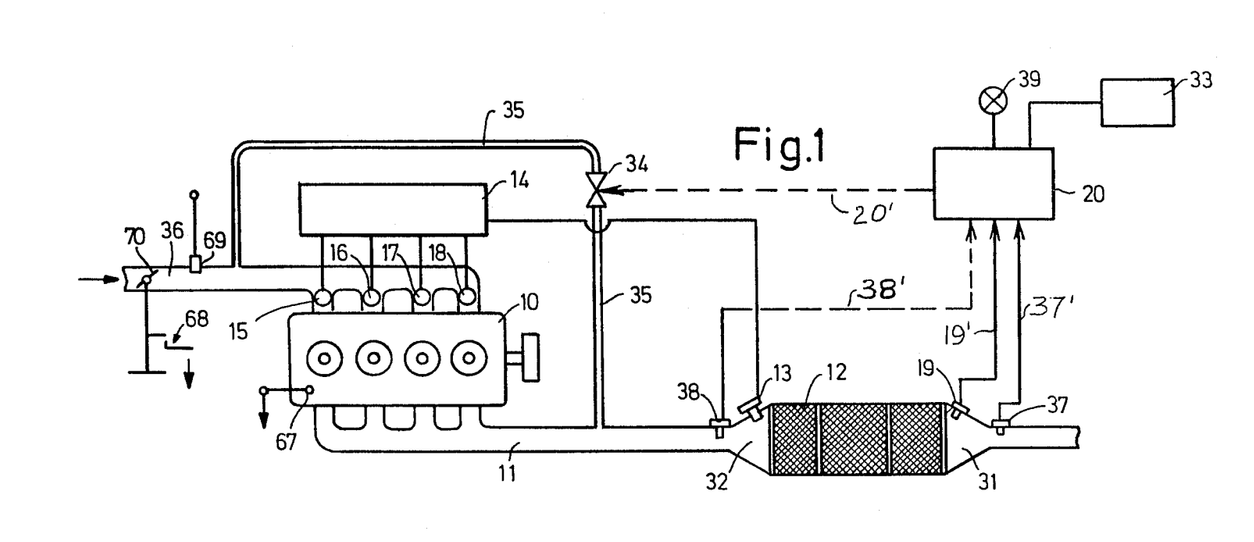
FIG. 1 is a schematic diagram of an internal combustion engine, and the monitoring system of the present invention.

An internal combustion engine 10 (FIG. 1) has an exhaust manifold 11 which is connected with a single-bed catalytic reactor 12. Single-bed catalytic reactors can effect detoxification efficiently if the mass ratio of the fuel-air mixture being supplied to the engine is properly controlled. This mass ratio of the fuel-air mixture is controlled by means of a sensor 13, located in the exhaust stream, which is connected to control the injection time of a fuel injection control system 14, operating fuel injection valves 15, 16, 17, 18, intermittently. The fuel injection control system 14 is, additionally, responsive to various operating parameters of the internal combustion engine and provides opening pulses to the injection valves 15–18 in dependence on these parameters which include the sensed composition of exhaust gases derived from sensor 13. A fuel injection control system is described in detail in the cross-referenced U.S. Pat. No. 3,483,851.

Figure 2:
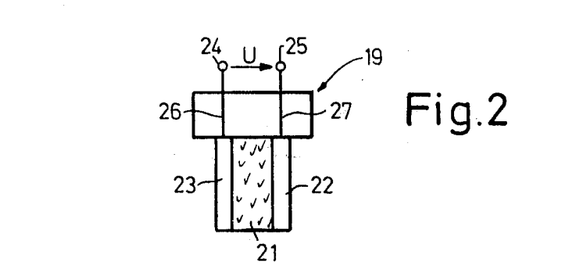
FIG. 2 is a highly schematic cross-sectional view of a suitable sensor.
Figures 3, 5:
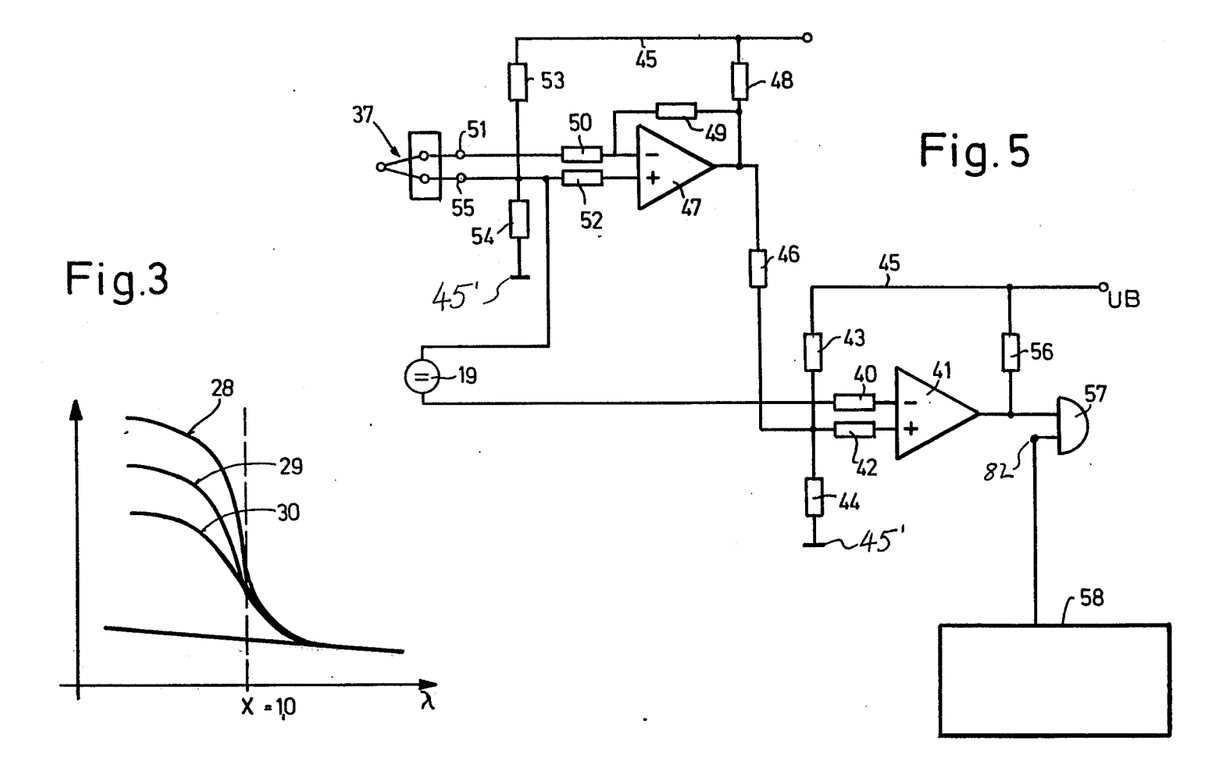
FIG. 3 is a series of graphs showing the output voltages of the sensor of FIG. 2 with respect to air number $\lambda$, in which the air number $\lambda$ represents the mass ratio of fuel to air and is unity when the ratio has the stoichiometric value.
FIG. 5 is a circuit diagram of a supervisory circuit to process the output signals from the sensor.

A sensor element, or sensor, for short, 19 is located in the catalytic reactor 12 at the downstream portion thereof. Sensor 19 is connected to a supervisory or monitor circuit 20. Sensor 19 may, for example, be constructed as illustrated in detail in FIG. 2. It includes an ion conductive solid electrolyte 21 to provide an oxygen concentration chain, for example made of zirconium dioxide, $ZrO_2$. A catalytically active material 22, for example platinum, and a catalytically inactive material 23, for example gold, are applied to the body of zirconium dioxide. The sensor of FIG. 2 permits determination of oxygen content of the exhaust gases, that is, that portion of oxygen which is present in the exhaust gases upon incomplete oxidation and thus not burned or present as oxygen compounds. The oxygen concentration chain has an approximately linear voltage curve upon change from a lean to a rich fuel-air mixture. The voltage difference can be determined at two terminals 24, 25 of the sensor 19 which, respectively, are connected over conductors 26, 27 with the layer of gold 23 and with the layer of platinum 22, respectively (see FIG. 2). The voltage appearing between terminals 24, 25, represented by the arrow U (FIG. 2) changes with respect to air number $\lambda$ as seen in the curves of FIG. 3, in which the air number $\lambda$ characterizes the ratio of fuel and air of the fuel-air mixture applied to the engine.

The voltage of the sensor also changes in dependence on the condition of the catalytic reactor. This can be readily seen when considering the curves of FIG. 3, in which the abscissa shows the air number $\lambda$ and the ordinate shows the voltage between terminals 24, 25. If the catalytic reactor 12 is completely inoperative, for example if the bed thereof is destroyed or poisoned, the voltage will be represented by curve 28. A poorly operating catalytic reactor will provide output voltages from sensor 19 as indicated by curve 29; a properly operating catalytic reactor 12 will provide output curves as shown at 30, FIG. 3. The difference in voltage relationships, with respect to air number, upon improper operation of the reactor, is governed by the presence of oxygen at the downstream side from the catalytic reactor 12. When the catalytic reactor 12 is operating properly (curve 30) only little remaining oxygen will appear downstream of the reactor 12. If the catalytic reactor bed is destroyed, however, there will be substantial remaining oxygen components in the exhaust gases, since the oxygen in the exhaust gases at the downstream side 31 of the catalytic reactor will have the same value as the oxygen being supplied to the upstream side 32 of the catalytic reactor 12. The voltage which depends on the condition of the catalytic reactor 12 is then connected by means of line 19' to the monitoring circuit 20 which operates, for example, an optical alarm device such as an indicator lamp 39 located on the dashboard of the vehicle, or on the control panel of the internal combustion engine. Lighting of indicator lamp 39 then indicates to the operator of the engine that the catalytic reactor needs repair or replacement. A holding or locking circuit 33 is provided, connected to the monitoring circuit 20 to prevent extinction of lamp 39 if it has once been operated, and holding lamp 39 in constantly illuminated condition if it is once energized. The holding circuit 33 may, for example, be a relay in a well known self-holding circuit, or having a mechanical lock and remaining locked, even if the control current to the relay is interrupted, until the relay is manually re-set. The re-setting of the relay can be interlocked with the reactor, for example requiring replacement of the reactor before the relay can be unlatched.

In many instances it is desirable to prevent operation of a vehicle with a defective catalytic reactor 12. To prevent such operation for an extended period of time, the monitoring circuit 20 has an output 20' which controls a transducer 34, in the simplest case a valve, located in an exhaust return line 35 from the exhaust 11 back to the inlet manifold of the engine 10. The exhaust feedback line 35 thus connects a portion of the exhaust gases, for example about 5 percent of the overall exhaust gases under idling conditions, back to the inlet manifold 36. Upon receiving an indication from sensor 19 that the catalytic reactor 12 operates poorly, or has been destroyed, monitoring circuit 20 will control valve 34, over line 20' to open valve 34 and return a portion of the exhaust gases back to the inlet manifold of the internal combustion engine. This substantially reduces the power output obtainable from the internal combustion engine and forces the operator to replace reactor 12 in the exhaust system in order to obtain normal power from the engine. This is a simple system and particularly effective if the feedback line 35 and valve 34 are already present in the vehicle, the valve 34 merely being provided with an additional control input connected to line 20'.

The output signal of sensor 19 is highly dependent on the temperature of the exhaust gases. A temperature sensor 37, connected to a line 37' is therefore provided downstream of the catalytic reactor to apply a temperature correction signal to the monitoring circuit 20 in order to modify processing of the output signals derived from sensor 19 in dependence on temperature.

The oxygen content in the exhaust from the internal combustion engine 10 is also determined by an providing an additional sensor element 38 at the upstream side 32 of the catalytic reactor 12, in addition to sensor 19 located at the downstream side of the reactor. Sensor 38 is connected over line 38' with monitoring circuit 20. The two sensors 19 and 38 which, preferably, are identical, provide respective signals representative of oxygen at the upstream side of the reactor 12 as well as at the downstream side of the reactor 12. Sensors 19, 38 then will provide difference signals which, provided that the exhaust gas temperature does not vary substantially during its passage through the catalytic reactor, provide a good indication and a measure of the operating effectiveness of the catalytic reactor 12. If the temperature difference between the upstream opening 32 and the downstream opening 31 of reactor 12 is substantial, use of temperature sensor 37 is desirable to compensate for temperature-dependent influences on the output signals of sensor 19, and 38, respectively. If the temperature does not vary substantially, then the temperature sensor 37 may be omitted.

Figure 4:
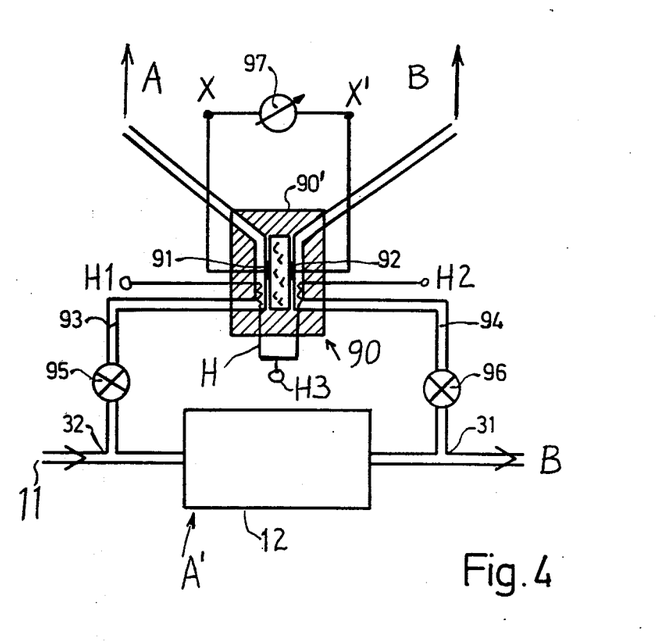
FIG. 4 is a schematic representation of a system to supervise the catalytic reactor.

The system utilizing two separate sensors 19, 38 can be simplified, as illustrated in FIG. 4, by using a single sensor 90 which has two catalytically inactive electrodes 91, 92 connected to the solid ion conductive body, for example zirconium dioxide, to measure the oxygen portion within the exhaust gases. A portion of the exhaust gases is guided past the first electrode 91, which is branched off from the upstream side 32 of the catalytic reactor 12. A portion of the exhaust gases from the downstream side 31 of the catalytic reactor 12 is guided past the second electrode 92 so that the ducts and electrodes form two cells. The sensor is so constructed that the geometry thereof is similar, and that it is symmetrical, so that there will be equality of size of the ducts for the exhaust gases, of speed of exhaust gases passing by the electrodes, and of temperature. The connection duct 93 upstream from the reactor has a valve 95 therein; the connection duct 94 downstream from the reactor has a valve 96 placed therein, so that the quantity of gases flowing past the electrodes can be controlled. The electrical signals taken off the two electrodes 91, 92 appear across terminals X, X', to be there applied to the monitoring circuit 20, to be processed as described. An indicating instrument 97, as shown in FIG. 4, may also be connected between terminals X, X'. The housing of the sensor 90 should be so constructed that there is good heat conduction between the electrodes 91, 92, as well as between the connecting lines 93, 94 of the exhaust gases, while the housing of the sensor 90, itself, is well insulated towards the outside, as shown at 90'. The amount of gases branched off can be very small, and the gases taken through line 93 can be exhausted into air as schematically indicated by arrow A or, if desired, the gases can be connected back to a branch inlet opening schematically indicated at A', FIG. 4, thereby avoiding exhaustion of any polluting gases into the atmosphere. The gases downstream of the reactor 12 and being passed through connection 94 can be exhausted directly to the atmosphere, as shown at B, or connected to suitable exhaust pipes, mufflers, or the like. Since these gases have already been treated by the catalytic reactor, they will be essentially free from polluting substances, provided the reactor 12 is functioning properly.

A hot wire detector H may be included within the portions of the ducts 93, 94 within the housing 90' of sensor 90. Hot wire detector H has two hot wires, the terminals of which are brought out at H1, H2 and H3, the latter being a common terminal for both hot wire detectors, in order to measure combustible components of the exhaust gases being applied to the reactor, and being exhausted from the reactor, respectively.

An actual circuit 20 is shown in FIG. 5, to operate an indicator lamp 39, or a transducer 34, if the reactor 12 should be essentially ineffective, or inoperative. Sensor 19 is connected over input resistor 40 to the inverting input of an operational amplifier 41, connected as a threshold switch; the non-inverting input is connected to a voltage divider formed by resistors 43, 44 connected across a source of supply UB, and connected to supply buses 45, 45'. The tap point of the voltage divider formed by the common junction of resistors 43, 44, connected over coupling resistor 42 to the non-inverting input of the operational amplifier 41, is also connected, over a coupling resistor 46, to the output of a second operational amplifier 47. Resistor 48 is connected from the output of unit 47 to positive bus 45. A resistor 49 connects the output of operational amplifier 47 to the inverting input thereof. The inverting input of the operational amplifier 47 is connected, through coupling resistor 50, to terminal 51 of the temperature sensor 37. The temperature sensor may, for example, be a thermal element, or an NTC resistor. The non-inverting input of operational amplifier 47 is connected over resistor 52 with the tap point of a voltage divider formed by resistors 53, 54 and connected across the supply source. Terminal 55 of temperature sensor 37 likewise connects to the tap point of the voltage divider 53, 54 which, further, is connected over coupling resistor 52 with the non-inverting input of the operational amplifier 47. The tap point is further connected to the other terminal of oxygen sensor 19.

Operation: If the voltage of sensor 19 drops below a certain threshold value, as determined by the setting of voltage divider resistors 43, 44, operational amplifier 41 will switch over and the output will have a 1-signal appear thereat, that is, it will, effectively, be connected to positive bus 45 over resistor 56. This 1-signal is connected to one input of an AND-gate 57. The second input of AND-gate 57 is connected to a scanning pulse source 58. Scanning pulse source 58 provides a 1-signal only if the internal combustion engine 10 has reached certain operating conditions, so that the AND-gate 57 can become activated only if these operating conditions actually arise. This ensures that measurement of the oxygen content in the exhaust gases is carried out at predetermined, definitely measurable operating conditions, so that masking of measuring results by changes in the operating condition of the internal combustion engine is effectively excluded. The scanning circuit is disclosed in detail in FIG. 7 and will be referred to below.

Temperature sensor 37, connected to operational amplifier 47 changes the voltage at the tap point of the voltage divider 43, 44 in dependence on the temperature of the exhaust gases. Influences on the output signal of sensor 19 due to temperature variations are thus compensated.

Figure 6:
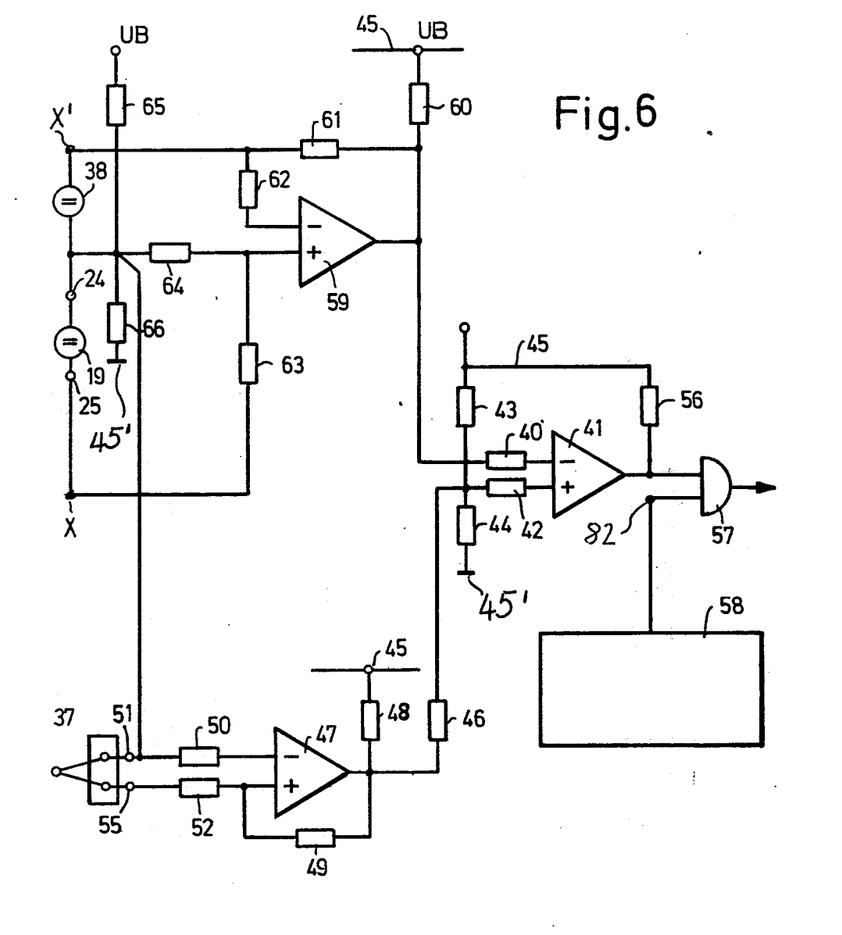
FIG. 6 is another circuit diagram of another embodiment of a supervisory circuit to process the output signals of the sensor of FIG. 2.

Embodiment of FIG. 6, in which components and circuits similar to those previously described have been given the same reference numerals and will not be described again: The essential difference between FIGS. 5 and 6 is that FIG. 5 is arranged for a single sensor 19, whereas FIG. 6 can be connected to two sensors 19, 38, or to the terminals X, X' of a dual sensing element, as described in connection with FIG. 4.

An operational amplifier 59 is connected as a reference circuit, the output of which is connected to the inverting input of the operational amplifier 41 over coupling resistor 40. The output of operational amplifier 59 is connected over load resistor 60 to positive bus 45 and, further, over resistor 61 to the input coupling resistor 62 and hence to the inverting input thereof. The junction of resistors 61, 62 is connected to one terminal of sensor 38, or to terminal X' of the dual unit of FIG. 4. The other terminal of sensor 38 is connected to the terminal 24 of sensor 19. The junction of the sensors 19, 38 is connected to the tap point of a voltage divider formed of resistors 65, 66 and over a coupling resistor 64 to the non-inverting input of the operational amplifier 59 which, further, is connected over coupling resistor 63 to the other terminal 25 of sensor 19 or to terminal X of the element of FIG. 4. The junction of the voltage dividers 65, 66 is likewise connected to terminal 51 of the temperature sensor 37 (if necessary) to compensate temperature influences. Sensor 37 and the circuit connections connected thereto determine if the temperature difference between the opening 32 in reactor 12 (FIG. 1) and the downstream opening 31 is in excess of a predetermined value. This compensation circuit, which uses the operational amplifier 47 is as previously described. The two sensors 19, 38 (or terminals X, X' of the element of FIG. 4) connected to the operational amplifier 59 apply the difference of the output signals of the sensors, or the sensing elements or sensing electrodes to the differential amplifier. If the output signal falls below a certain value determined by the setting of the tap point of the voltage dividers 65, 66, which provides a threshold level, then operational amplifier 41 will switch over and the input of AND-gate 57 will have a 1-signal applied which will become conductive if the scanning signal generator 58 provides its output signal. The output from AND-gate 57 operates the alarm indicator 39 and, if used, the transducer 34. If the element of FIG. 4 is used, then the circuit will be identical except that the connection between the elements 38, 19 will be inherent in the unit itself and there will be no connection to the tap point of the voltage dividers 65, 66. A center electrode may be provided on the unit of FIG. 4 is such a connection is desirable.

Figure 7:
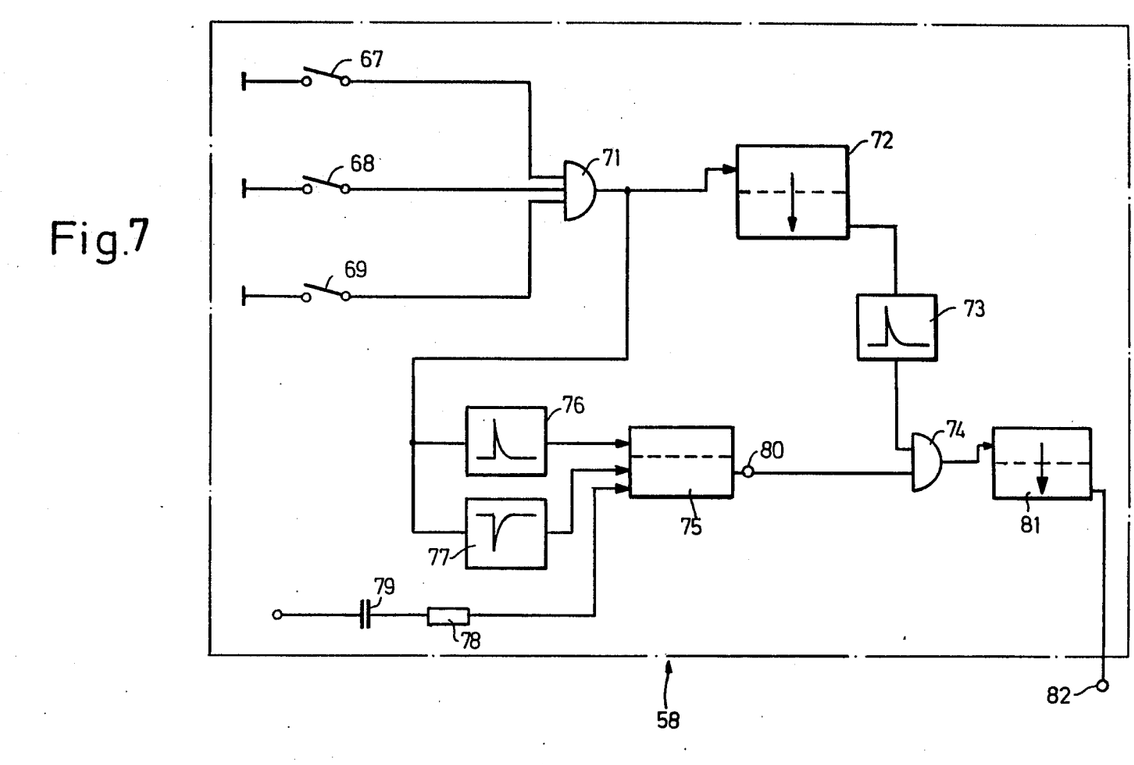
FIG. 7 is a schematic circuit diagram to operate the supervisory system in dependence on various operating parameters of the internal combustion engine.

The scanning signal generator 58 is shown in FIG. 7. A predetermined operating condition of the internal combustion engine is determined thereby, so that the oxygen content in the exhaust gases will be measured for a certain time, depending on the operating condition, permitting the circuit 20 to become effective if the result of the measurement, as determined by the oxygen sensors, indicates that the catalytic reactor is defective or inoperative. The scanning circuit generator 58 has three transducer inputs 67, 68, 69. Transducer input 67 is a temperature-dependent switch which provides an output signal if the temperature of the engine has reached a certain predetermined value. Transducer 68 is a throttle switch which provides an output signal if the throttle 70 (FIG. 1) in the induction system to the engine has a predetermined position. Transducer 69 is a vacuum switch, located in the intake manifold of the engine and providing an output signal when a certain vacuum is sensed in the inlet manifold. All three transducers (schematically shown in FIG. 1, and indicated merely as switches in FIG. 7) are connected to respective inputs of an AND-gate 71. The output of this AND-gate is connected with the input of a monostable flip-flop (FF) 72, which is connected over a differentiating circuit 73 with the first input of an AND-gate 74. The second input of the AND-gate 74 is connected to the output of a bistable FF 75. Bistable FF 75 has one input connected to a first differentiator 76, a second input connected to the output of a second differentiator 77. The inputs to the differentiators 76, 77 are connected to the output of the AND-gate 71. A resistor 78 and a capacitor 79, forming a trigger circuit, are further connected to the ignition switch for the internal combustion engine 10. When the ignition switch is operated, a pulse applied over the R/C circuit 78, 79 re-sets bistable FF 75 to its OFF or RE-SET condition, providing an output at its output terminal 80 representing a ZERO, so that the second input of AND-gate 74 will normally have a 0-signal applied. The output of the AND-gate 74 is connected to a monostable FF 81, the output terminal 82 of which connects to the second input of the AND-gate 57 of FIGS. 5 and 6.

Operation: When the internal combustion engine has certain operating conditions, that is, when all three transducers 67, 68, 69 provide a 1-signal, the output of the AND-gate 71 will have a 1-signal applied. Occurrence of the 1-signal, differentiated over differentiator 76, triggers FF 75 into SET state. Further, FF 72 is triggered into unstable condition. Output terminal 80 of FF 75 will now have a 1-signal applied to the second input of the AND-gate 74. When bistable FF 75 remains connected during the unstable time of the monostable FF 72, that is, if during this time output terminal 80 has a 1-signal applied thereat, monostable FF 72, upon re-set, can apply a signal over AND-gate 74 to change monostable FF 81 into unstable state. When monostable FF 81 is unstable, output signal 82 will have a 1-signal appear thereat, connected to the second input of the AND-gate 57 (FIGS. 5, 6). AND-gate 58 will become conductive and, dependent on the output signal of sensor 19, or sensors 19 and 38, or sensor 90, an output signal will be derived from AND-gate 57 to trigger or energize the alarm 39, and/or the transducer 34.

If one of the three transducers 67, 68, 69 has a 0-signal, that is, upon change in operating condition of the internal combustion engine 10, bistable FF 75 will be triggered into RE-SET state, so that the signal at terminal 80 will fail and the second input of the AND-gate will have a 0-signal applied thereat. Circuit 20 (FIG. 1) is thus entirely disconnected and the optical warning system 39, or transducer 34 can no longer be triggered. Differentiators 76, 77 set or re-set, respectively, FF 75 upon occurrence of the respective pulses. Connection of positive, or negative pulses can be selected by suitably connected and properly polarized diodes. FF 81 is triggered upon re-set of the FF 72, as indicated by the connection of differentiator 73 to the complementary output of FF 72.

A warning device is energized, and/or the performance of the internal combustion engine is affected if the output signal of sensor 19, or 19 and 38, or 90 indicates deterioration of effectiveness of the catalytic reactor 12. The operator, therefore, is warned that the operating characteristics of the engine no longer meet exhaust emission requirements, and, desirably, the operating performance of the vehicle is effected to such an extent that the operator is forced to have the defective reactor repaired, or replaced.

Various changes and modifications may be made within the scope of the inventive concept, and features described in connection with any one embodiment may, likewise, be used with any other embodiment.

Typical operating conditions which cause closing of the switches 67, 68, 69 are:

switch 67 — engine operating temperature above a certain level, that is, at engine operating level.
switch 68: throttle at idle position
switch 69: maximum vacuum under proper idle conditions of the engine;

alternatively, switches 68, 69 could be set to operate so that switch 68 closes when the throttle is wide open, and the switch 69 responds to an intermediate value of vacuum, indicating full load operation without, however, overloading, or excessive loading.

The sensor of FIG. 4 may also use only hot wires, the elements of the hot wires being placed in the respective ducts 93, 94, which can be insulated from each other, thus eliminating the electrolyte core and electrodes 91, 92 connected thereto. Terminals H1, H2 can then be connected to the circuit of FIG. 6 at points X, X1, and terminal H3 can be connected at the junction between resistors 65, 66.

We claim:
1. Catalytic reactor monitoring system to supervise operation of a catalytic reactor (12) connected to the exhaust system of an internal combustion engines, to detoxify exhausted gases from the engine, comprising
at least two oxygen sensor elements (19, 38), one exposed to exhaust gases upstream, and the other downstream of the reactor (12) to respectively determine oxygen content in the exhaust gases from the internal combustion engine upstream, and downstream of the reactor each including an ion conductive solid electrolyte (21) forming an ion concentration chain;
a detection circuit (20) including a difference circuit having its respective terminal connected to the respective sensor elements to determine the difference in output signals from the sensor elements
and response means (39, 34) responsive to the output signal from the detection circuit (20).
2. System according to claim 1, wherein the catalytic reactor (12) is formed with an opening at the downstream end thereof and the downstream sensor element (19) is located in said opening.
3. System according to claim 1, further comprising a temperature sensor (37) in temperature sensing relationship to the temperature of the catalytic reactor (12) and providing an output signal applied to the detection circuit (20) to compensate temperature depending changes in the output signals from the sensor elements (19, 38).
4. System according to claim 1, wherein the solid electrolyte of each sensor element having a catalytically inactive material (23) and a catalytically active material (22) applied thereto and forming contacts therewith, the voltages (U) appearing between said materials being connected to the respective terminals of the difference circuit (59).
5. System according to claim 1, wherein the detection circuit further includes a threshold switch (41); and
a temperature sensor (37) in temperature sensing relationship to the reactor (37), the output of the difference circuit (59) being connected to one input of the threshold switch (41), and the output of the temperature sensor (37) being connected to the other input of the threshold switch (41).

6. System according to claim 1, further comprising a temperature sensor (37) located in temperature sensing relationship to the reactor 12;

and an amplifier (47) connecting the temperature sensor (37) to the detection circuit (20).

7. System according to claim 1, wherein the detection circuit (20) comprises a threshold switch (41) providing an output if, and only if the downstream sensor element (19) provides an output signal indicative of oxygen levels in the exhaust gases downstream of the reactor (12) above a predetermined level;

a gating circuit (57) is provided, and means (58) gating said gating circuit (57) ON in dependence on an operating condition of the internal combustion engine, said gating circuit being interposed between the detection circuit (20) and said response means (39, 34).

8. System according to claim 1, wherein the response means comprises a humanly perceptible alarm indicator (39).

9. System according to claim 1, wherein said response means comprises transducer means connected to the engine to affect operation of the engine tending to decrease its performance to provide an indication that the detection circuit (20) has detected a difference in output from the sensor elements indicative of malfunction of the reactor (12).

10. System according to claim 9, wherein an exhaust feedback line (35) is provided branching exhaust gases to the inlet manifold of the internal combustion engine (10);

and the transducer means comprises a valve (34) effective to control communication of gases through said feedback line.

11. System according to claim 1, further comprising a holding or latching device (33) connected to the detection circuit (20) and preventing drop-out of the response means (39, 34) if the detection circuit has once detected a difference in output from the sensor elements indicative of malfunction of the reactor (12).

12. System according to claim 7, further comprising scanning signal generator means (58) and transducer means (67, 68, 69), responsive to operating conditions or parameters of the engine (10), the transducer means controlling the scanning signal generator means to provide a scanning pulse upon occurrence of predetermined operating conditions, as sensed by said transducer means, to command the scanning signal generator means to provide a scanning signal to said gating circuit (57) to open the gating circuit and permit connections of signals from the detection circuit (20) to the response means (34, 39) to normalize, or standardize monitoring of composition of exhaust gases passed through the reactor (12) to predetermined operating conditions of the engine.

* * * * *